US011161888B2

(12) United States Patent
Park et al.

(10) Patent No.: US 11,161,888 B2
(45) Date of Patent: Nov. 2, 2021

(54) METHOD FOR REGULATING TARGETING OF CYCLIN Y (CCNY) PROTEIN TO SYNAPSES

(71) Applicant: KOREA INSTITUTE OF SCIENCE AND TECHNOLOGY, Seoul (KR)

(72) Inventors: Mikyoung Park, Seoul (KR); Yuri Choi, Seoul (KR); Jung-hwa Hong, Seoul (KR); Eunsil Cho, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 0 days.

(21) Appl. No.: 16/666,607

(22) Filed: Oct. 29, 2019

(65) Prior Publication Data

US 2020/0140507 A1    May 7, 2020

(30) Foreign Application Priority Data

Nov. 2, 2018  (KR) .......................... 10-2018-0133852

(51) Int. Cl.
*C07K 14/47* (2006.01)
*C12N 15/87* (2006.01)

(52) U.S. Cl.
CPC .......... *C07K 14/4738* (2013.01); *C12N 15/87* (2013.01); *C07K 2319/033* (2013.01)

(58) Field of Classification Search
CPC ...................... C07K 14/4738; C07K 2319/033
See application file for complete search history.

(56) References Cited

FOREIGN PATENT DOCUMENTS

KR        20170010521 A    2/2017

OTHER PUBLICATIONS

Brigidi et al. Activity-regulated trafficking of the palmitoyl-acyl transferase DHHC5. Nat Commun 6, 8200 (2015).*
Alaa E. El-Husseini, et al., "Dual Palmitoylation of PSD-95 Mediates Its Vesiculotubular Sorting, Postsynaptic Targeting, and Ion Channel Clustering", The Journal of Cell Biology, vol. 148, No. 1, Jan. 10, 2000 159-171.
Alaa El-Din El-Husseini, et al., "Protein Palmitoylation:A Regulator of Neuronal Development and Function", Nature Reviews:NEUROSCIENCE, vol. 3, Oct. 2002, 791-802.
Alaa El-Din El-Husseini, et al., "Synaptic Strength Regulated by Palmitate Cycling on PSD-9", Cell, vol. 108, 849-863, Mar. 22, 2002.
Chan-Yen Ou, et al., Two cyclin-dependent kinase pathways are essential for polarized trafficking of presynaptic components. Cell. May 28, 2010; 141(5): 846-858. doi:10.1016/j.cell.2010.04.011.
Dongmei Liu, et al., Cyclin Y Is a Novel Conserved Cyclin Essential for Development in *Drosophila*, Genetics 184: 1025-1035 (Apr. 2010).

Eric Schnell, Direct interactions between PSD-95 and stargazin control synaptic AMPA receptor number, PNAS, Oct. 15, 2002, vol. 99, No. 21, 13902-13907.
Eunsil Cho, et al., "Cyclin Y inhibits plasticity-induced AMPA receptor exocytosis and LTP", Scientific Reports, 5:12624, DOI: 10.1038/srep12624, 13 pages. 2015.
Eunsil Cho, et al., Palmitoylation in Alzheimer's disease and other neurodegenerative diseases.Pharmacological Research 111 (2016) 133-151.
Ingrid Ehrlich, et al., "Postsynaptic Density 95 collrols AMPA Receptor Incorporation during Long-Term Potentiation and Experience-Driven Synaptic Plasticity", J. Neurosci., Jan. 28, 2004, 24(4):916-927.
I-Seul Joe, et al., Cyclin Y-mediated transcript profiling reveals several important functional pathways regulated by Cyclin Y in hippocampal neurons, PLoS ONE 12(2): e0172547 . doi:10.1371/journal.pone.0172547, Feb. 27, 2017, pp. 1-16.
J. Rick Topinka, et al., N-Terminal Palmitoylation of PSD-95 Regulates Association with Cell Membranes and Interaction with K+ Channel Kv1.4, Neuron, vol. 20, 125-134, Jan. 1998.
Jean-Claude Beique, et al., Synapse-specific regulation of AMPA receptor function by PSD-95, PNAS Dec. 19, 2006, vol. 103, No. 51, 19535-19540.
Jian Ren, et al., CSS-Palm 2.0: an updated software for palmitoylation sites prediction, Protein Engineering, Design & Selection vol. 21 No. 11 pp. 639-644, 2008.
Junmei Wan, et al., Palmitoylated proteins: purification and identification, Nature Protocols , vol. 2 No. 7, 2007, 1573-1584.
Kun Huang, et al., Modulation of neuronal protein trafficking and function by palmitoylation, Current Opinion in Neurobiology 2005, 15:527-535.
Liyong Zeng, et al., Essential Roles of Cyclin Y-Like 1 and Cyclin Y in Dividing Wnt-Responsive Mammary Stem/Progenitor Cells, PLoS Genet 12(5): e1006055.doi:10.1371/journal.pgen.1006055, May 20, 2016, pp. 1-21.
Lucas Matt, et al., Role of Palmitoylation of Postsynaptic Proteins in Promoting Synaptic Plasticity, Frontiers in Molecular Neuroscience, Jan. 2019 | vol. 12 | Article 8, 19 pages.
Martin E. M. Noble, et al., The cyclin box fold: protein recognition in cell-cycle and transcription control, TIBS 22, Dec. 1997, 482-487.
Mei Jiang, et al., Cyclin Y, a novel membrane-associated cyclin, interacts with PFTK1, FEBS Letters 583 (2009) 2171-2178.

(Continued)

*Primary Examiner* — Gregory S Emch
(74) *Attorney, Agent, or Firm* — Cantor Colburn LLP (57) ABSTRACT

The present invention relates to a method for regulating localization of CCNY protein to synapses, comprising palmitoylation of CCNY protein. Specifically, the present invention relates to a method for regulating targeting of CCNY protein to synapses by regulating addition of a palmitoyl group to cysteine at position 7 and/or 8 on the CCNY protein. Therefore, the palmitoylation of CCNY, a postsynaptic protein known to be implicated in synaptic plasticity and learning and memory, is a critical process for CCNY to be localized in postsynaptic spines, and thus it can be found that CCNY plays an important role in synaptic functions.

3 Claims, 5 Drawing Sheets
(4 of 5 Drawing Sheet(s) Filed in Color)

Specification includes a Sequence Listing.

(56) References Cited

OTHER PUBLICATIONS

Mikyoung Park, et al., CYY-1/Cyclin Y and CDK-5 Differentially Regulate Synapse Elimination and Formation for Rewiring Neural Circuits, Neuron. May 26, 2011; 70(4): 742-757. doi:10.1016/j.neuron.2011.04.002.

Takashi Hayashi, et al., Differential Regulation of AMPA Receptor Subunit Trafficking by Palmitoylation of Two Distinct Sites, Neuron, vol. 47, 709-723, Sep. 1, 2005, DOI 10.1016/j.neuron.2005.06.035.

Tom Evans, et al., Cyclin: A Protein Specified by Maternal mRNA in Sea Urchin Eggs That Is Destroyed at Each Cleavage Division, Cell, vol. 33, 389-396, Jun. 1983.

Wentao Yue, et al., Cell Cycle Protein Cyclin Y Is Associated With Human Non-Small-Cell Lung Cancer Proliferation and Tumorigenesis, Clinical Lung Cancer, vol. 12, No. 1, 43-50, 2011; DOI: 10.3816/CLC.2011.n.006.

YongGang Xu, et al., Lentivirus-Mediated Knockdown of Cyclin Y (CCNY) Inhibits Glioma Cell Proliferation, Oncology Research, vol. 18, pp. 359-364, 2010.

Yuko Fukata, et al., Protein palmitoylation in neuronal development and synaptic plasticity, Nature Reviews, Neuroscience, 2010, vol. 11, Mar. 2010, 161-175.

Matthew James Edmonds, A systematic study of palmitoylation using the model organism Caenorhabditis elegans, Ph.D. Thesis, the University of Liverpool, Apr. 2013, 255 pp.

B. Alex Merrick, et al., Proteomic Profiling of S-acylated Macrophage Proteins Identifies a Role for Palmitoylation in Mitochondrial Targeting of Phospholipid Scramblase 3* Molecular & Cellular Proteomics 10 : 10.1074/mcp.M110.006007, 1-13, 2011, 13 pp.

Kumari B, et al. (2014) PalmPred: An SVM Based Palmitoylation Prediction Method Using Sequence Profile Information. PLoS ONE 9(2):e89246. doi:10.1371/journal.pone.0089246 (10 pages).

NCBI Reference Sequence : NP_001178762.1, Jun. 1, 2018.

* cited by examiner

| [CCNY] | | |
|---|---|---|
| Position | Peptide | Score |
| 7 | MGNTTSCCVSSSPK | 13.556 |
| 8 | MGNTTSCCVSSSPKL | 43.137 |
| 39 | LSREDTGCNLQHISD | 4.491 |
| 101 | TSRKYSSCSTIFLDD | 6.376 |
| 122 | NLKYTIKCVALAIYY | 4.718 |
| 188 | AAQLTAECAIVTLVY | 3.341 |
| 208 | TYAEIDICPANWKRI | 0.602 |
| 238 | AVWNVDYCQILKDIT | 1.333 |
| 309 | LEAISRLCEDKYKDL | 1.575 |

| [PSD-95] | | |
|---|---|---|
| Position | Peptide | Score |
| 3 | MDCLCIVTTK | 17.28 |
| 5 | MDCLCIVTTKKY | 41.463 |
| 445 | DYDKTKDCGFLSQAL | 6.955 |
| 562 | FPDKFGSCVPHTTRP | 6.13 |
| 626 | VAEQGKHCILDVSAN | 2.666 |
| 687 | LEQEFTECFSAIVEG | 4.518 |

B

C

Scale bars, 20 μm

SEQUENCE LISTING

<160> NUMBER OF SEQ ID NOS: 7

<210> SEQ ID NO 1
<211> LENGTH: 341
<212> TYPE: PRT
<213> ORGANISM: Caenorhabditis elegans

<400> SEQUENCE: 1

Met Gly Asn Thr Thr Ser Cys Cys Val Ser Ser Ser Pro Lys Leu Arg
1               5                   10                  15

Arg Asn Ala His Ser Arg Leu Glu Ser Tyr Arg Pro Asp Thr Asp Leu
            20                  25                  30

Ser Arg Glu Asp Thr Gly Cys Asn Leu Gln His Ile Ser Asp Arg Glu
         35                  40                  45

Asn Ile Asp Asp Leu Asn Met Glu Phe Asn Pro Ser Asp His Pro Arg
 50                  55                  60

Ala Ser Thr Ile Phe Leu Ser Lys Ser Gln Thr Asp Val Arg Glu Lys
 65                  70                  75                  80

Arg Lys Ser Leu Phe Ile Asn His His Pro Pro Gly Gln Thr Ser Arg
                 85                  90                  95

Lys Tyr Ser Ser Cys Ser Thr Ile Phe Leu Asp Asp Ser Thr Val Ser
                100                 105                 110

Gln Pro Asn Leu Lys Tyr Thr Ile Lys Cys Val Ala Leu Ala Ile Tyr
                115                 120                 125

Tyr His Ile Lys Asn Arg Asp Pro Asp Gly Arg Met Leu Leu Asp Ile
            130                 135                 140

Phe Asp Glu Asn Leu His Pro Leu Ser Lys Ser Glu Val Pro Pro Asp
145                 150                 155                 160

Tyr Asp Lys His Asn Pro Glu Gln Lys Gln Ile Tyr Arg Phe Val Arg
                165                 170                 175

Thr Leu Phe Ser Ala Ala Gln Leu Thr Ala Glu Cys Ala Ile Val Thr
            180                 185                 190

Leu Val Tyr Leu Glu Arg Leu Leu Thr Tyr Ala Glu Ile Asp Ile Cys
                195                 200                 205

Pro Ala Asn Trp Lys Arg Ile Val Leu Gly Ala Ile Leu Leu Ala Ser
            210                 215                 220

Lys Val Trp Asp Asp Gln Ala Val Trp Asn Val Asp Tyr Cys Gln Ile
225                 230                 235                 240

Leu Lys Asp Ile Thr Val Glu Asp Met Asn Glu Leu Glu Arg Gln Phe
                245                 250                 255

Leu Glu Leu Leu Gln Phe Asn Ile Asn Val Pro Ser Ser Val Tyr Ala
                260                 265                 270

Lys Tyr Tyr Phe Asp Leu Arg Ser Leu Ala Glu Ala Asn Ser Leu Ser
            275                 280                 285

Phe Pro Leu Glu Pro Leu Ser Arg Glu Arg Ala His Lys Leu Glu Ala
290                 295                 300

Ile Ser Arg Leu Cys Glu Asp Lys Tyr Lys Asp Leu Arg Lys Pro Met
305                 310                 315                 320

Arg Lys Arg Ser Ala Ser Ala Asp Asn Leu Ile Leu Pro Arg Trp Ser
                325                 330                 335

Pro Ala Ile Ile Ser
            340

<210> SEQ ID NO 2
<211> LENGTH: 37
<212> TYPE: DNA
<213> ORGANISM: artificial sequence
<220> FEATURE:
<223> OTHER INFORMATION: CCNY-C7S-EGFP F primer

<400> SEQUENCE: 2
cttagggctg gacgacacgc aggacgaagt tgtgttc                    37

<210> SEQ ID NO 3
<211> LENGTH: 37
<212> TYPE: DNA
<213> ORGANISM: artificial sequence
<220> FEATURE:

```
<223> OTHER INFORMATION: CCNY-C7S-EGFP R primer

<400> SEQUENCE: 3
cttagggctg gacgacacgc aggacgaagt tgtgttc                              37

<210> SEQ ID NO 4
<211> LENGTH: 37
<212> TYPE: DNA
<213> ORGANISM: artificial sequence
<220> FEATURE:
<223> OTHER INFORMATION: CCNY-C8S-EGFP F primer

<400> SEQUENCE: 4
gaacacaact tcgtgctccg tgtcgtccag ccctaag                              37

<210> SEQ ID NO 5
<211> LENGTH: 37
<212> TYPE: DNA
<213> ORGANISM: artificial sequence
<220> FEATURE:
<223> OTHER INFORMATION: CCNY-C8S-EGFP R primer

<400> SEQUENCE: 5
cttagggctg gacgacacgg agcacgaagt tgtgttc                              37

<210> SEQ ID NO 6
<211> LENGTH: 37
<212> TYPE: DNA
<213> ORGANISM: artificial sequence
<220> FEATURE:
<223> OTHER INFORMATION: CCNY-C7,8S-EGFP F primer

<400> SEQUENCE: 6
gaacacaact tcgtcctccg tgtcgtccag ccctaag                              37

<210> SEQ ID NO 7
<211> LENGTH: 37
<212> TYPE: DNA
<213> ORGANISM: artificial sequence
<220> FEATURE:
<223> OTHER INFORMATION: CCNY-C7,8S-EGFP R primer

<400> SEQUENCE: 7
cttagggctg gacgacacgg aggacgaagt tgtgttc                              37
```

METHOD FOR REGULATING TARGETING OF CYCLIN Y (CCNY) PROTEIN TO SYNAPSES

This application claims priority to Korean Patent Application No. 10-2018 0133852, filed Nov. 2, 2018, and all the benefits accruing therefrom under 35 U.S.C. § 119, the content of which in its entirety is herein incorporated by reference.

SEQUENCE LISTING

This application includes a sequence listing submitted as an ASCII text file created Jan. 7, 2019, named 8GI0537.TXT and having a file size of 4.3 Kb; the sequence listing is incorporated by reference herein.

TECHNICAL FIELD

The present invention relates to a method for regulating localization of CCNY protein to synapses, including palmitoylation of CCNY protein. Specifically, the present invention relates to a method for regulating targeting of CCNY protein to synapses by regulating addition of a palmitoyl group to cysteine at position 7 and/or 8 on the CCNY protein.

BACKGROUND ART

Palmitoylation is a post-translational lipid modification involving the attachment of a 16-carbon palmitate to a cysteine residue of a protein via a thioester bond (Fukata and Fukata, 2010; Cho and Park, 2016). It has been well described as influencing a large number of neuronal proteins in multiple aspects, including their trafficking and localization, structure and stability, and protein-protein interactions, ultimately increasing the functional complexity in the nervous system (El-Husseini et al., 2000; El-Husseini and Bredt, 2002; Hayashi et al., 2005; Huang and El-Husseini, 2005; Yanai et al., 2006; Fukata and Fukata, 2010).

PSD-95 (postsynaptic density of 95 kDa) is a representative scaffolding protein located beneath the postsynaptic membrane of synapses and having an electron-dense structure highly concentrated with important structural and signaling proteins (Kim and Sheng, 2009). PSD-95 is a representative palmitoylated synaptic protein (Topinka and Bredt, 1998; El-Husseini et al., 2000; El-Husseini et al., 2002; El-Husseini and Bredt, 2002), exerting its function in synapse formation and synaptic plasticity and in various neuronal functions (Schnell et al., 2002; Ehrlich and Malinow, 2004; Beique et al., 2006).

Meanwhile, Cyclin Y (CCNY) belongs to the cyclin family, which is known to regulate cell cycle and transcription (Evans et al., 1983; Noble et al., 1997). CCNY was first described as an interactive protein with cyclin-dependent kinase CDK14/PFTK1 using yeast two-hybrid assay (Jiang et al., 2009), and further studies revealed that CCNY has a role in the proliferation of glioma and lung cancer cells (Xu et al., 2010; Yue et al., 2011), developmental processes in *Drosophila* (Liu and Finley, 2010), and cell cycle progression and maintenance of mammary stem/progenitor cell properties (Zeng et al., 2016).

The roles of CCNY in neuronal function were described initially in the nervous system of the nematode *Caenorhabditis elegans*, revealing its regulatory role in the proper localization of synaptic proteins (Ou et al., 2010) and in the remodeling of neural circuits by modulating synapse elimination and formation (Park et al., 2011).

Recently, CCNY has also been shown to regulate hippocampal long-term potentiation (LTP) (Cho et al., 2015), a form of synaptic plasticity known to be the cellular basis of learning and memory. In addition, a transcriptome analysis identified several important functional pathways that are regulated by CCNY in hippocampal neurons, including learning and memory, synaptic plasticity, and the actin cytoskeleton (Joe et al., 2017).

With this background, the present inventors found that CCNY, a novel postsynaptic protein, is localized in close proximity to the PSD due to palmitoylation of CCNY at its two cysteine residues at cysteine 7 (C7) and C8, and confirmed that CCNY is located in synaptic regions through the palmitoylation-mediated association with the plasma membrane, where CCNY functions, thereby completing the present invention.

DISCLOSURE

Technical Problem

It is one object of the present invention to provide a method for regulating the localization of CCNY protein to synapses, including palmitoylation of CCNY protein.

It is another object of the present invention to provide a method for preventing or treating a cognitive disease, including substituting at least one cysteine residue in the amino acid sequence constituting CCNY protein with another amino acid.

It is still another object of the present invention to provide a method for enhancing memory, including substituting at least one cysteine residue in the amino acid sequence constituting CCNY protein with another amino acid.

Technical Solution

In order to achieve the above objects, one aspect of the present invention provides a method for regulating the localization of CCNY protein to synapses, including palmitoylation of CCNY protein.

Another aspect of the present invention provides a method for preventing or treating a cognitive disease, including substituting at least one cysteine residue in the amino acid sequence constituting CCNY protein with another amino acid.

Still another aspect of the present invention provides a method for enhancing memory, including substituting at least one cysteine residue in the amino acid sequence constituting CCNY protein with another amino acid.

Hereinafter, the present invention will be described in detail.

As used herein, the term "CCNY (Cyclin Y)" is one member of the cyclin family known to have a role in regulating the cell cycle and transcription, and several studies on CCNY have been reported in the field of cancer biology.

In previous studies, the present inventors found that the CCNY protein is involved in synapse remodeling in *Caenorhabditis elegans*, and is localized postsynaptically in mammals. In addition, it has been shown that exocytosis of AMPA receptors during long-term potentiation, which is the cellular basis of learning and memory, is promoted when CCNY function is reduced by inhibiting the expression of CCNY.

Accordingly, based on these studies, the present inventors have newly found through further experimentation that the postsynaptic localization step of CCNY protein, where the CCNY protein exhibits its function, can be regulated when palmitoylation of CCNY is regulated, and have also newly confirmed that it is possible to treat a cognitive disease or enhance memory by altering postsynaptic localization of CCNY protein even if a CCNY inhibitor is not used.

The subject including the CCNY protein may specifically be mammals including humans, dogs, pigs, etc. without limitation.

The CCNY protein may have an amino acid sequence of SEQ ID NO: 1, and the amino acid sequence of SEQ ID NO: 1 may specifically include a sequence having homology of at least 80% or more, more specifically a sequence having homology of at least 85% or more, even more specifically a sequence having homology of at least 90% or more, and even further more specifically a sequence having homology of at least 95% or more, without limitation.

In addition, the sequence of SEQ ID NO: 1 may include a sequence having substitution, deletion, or modification of a part of the sequence, and any sequence may be included as long as it exhibits activity as CCNY protein.

As used herein, the term "palmitoylation" refers to the addition of a palmitoyl group to a cysteine residue present at a specific position of a substrate protein, specifically refers to the addition of a palmitoyl group to at least one cysteine residue in the amino acid sequence of the CCNY protein, and more specifically refers to the addition of a palmitoyl group to at least one cysteine residue in the amino acid sequence of SEQ ID NO: 1.

The addition of a palmitoyl group to a cysteine residue in the amino acid sequence of the CCNY may include treatment with enzymes, etc. that can add a palmitoyl group. Specifically, the enzyme may include enzymes capable of delivering a palmitoyl group, more specifically palmitoyl acyltransferases (PATs; also called DHHC enzymes due to the inclusion of an Asp-His-His-Cys motif), but is not limited thereto.

Figure 3:
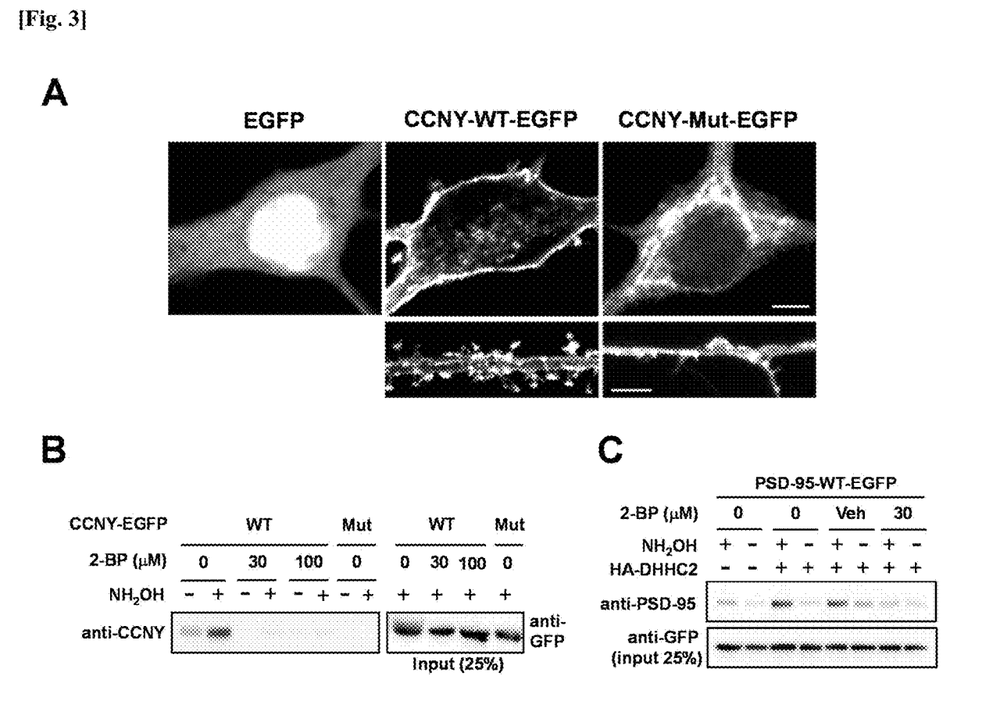

In one specific embodiment of the present invention, among DHHC2, DHHC3, DHHC7, DHHC8, DHHC15, and DHHC17, which are known as palmitoyl acyltransferases that palmitoylate PSD-95 protein, DHHC2 was used (FIG. 3). Therefore, it can be inferred therefrom that the presence of the palmitoyl acyltransferase that palmitoylates CCNY is confirmed, and that the palmitoylation of CCNY can be achieved by treating the CCNY protein with the palmitoyl acyltransferase.

As used herein, the term "palmitoyl transferase" refers to an enzyme that catalyzes a reaction whereby a saturated fatty acid palmitate is added to a cysteine residue of the target substrate protein via a thioester bond.

As used herein, the term "palmitoyl" has a chemical formula of $C_{16}H_{31}O$ and a molecular weight of 239.423 g/mol. It is called hexadeca-1-ol according to IUPAC nomenclature and consists of 31 hydrogen atoms, 16 carbon atoms, and one oxygen atom.

As used herein, the term "cysteine" is a type of sulfur-containing amino acid having a molecular formula of $C_3H_7NO_2S$ and a molecular weight of 121 g/mol.

As used herein, the term "other amino acid" refers to an amino acid other than cysteine, and specifically includes, but is not limited to, serine or alanine.

As used herein, the term "serine" refers to an organic compound having a chemical formula of $HO_2CCH(NH_2)CH_2OH$, which is one of the 20 amino acids, and is classified as a non-essential amino acid. It has been shown to be synthesized from other metabolites in the body such as glycine.

As used herein, the term "alanine" refers to an organic compound having a chemical formula of $C_3H_7NO_2$. The L-isomer of alanine is one of the 20 amino acids constituting proteins and is abbreviated as "A". It is generally known to be produced by the reductive amination of pyruvic acid, and has been reported as a non-essential amino acid that is closely linked to metabolic pathways such as glycolysis, gluconeogenesis, and the citric acid cycle.

In the present invention, the novel method that regulates the localization of CCNY protein to synapses was confirmed to be due to palmitoylation, whereby a palmitoyl group is added to at least one cysteine residue in the amino acid sequence constituting the CCNY protein. Specifically, the cysteine residue may be at position 7 and/or 8 in the amino acid sequence constituting the CCNY protein.

In the present invention, the CCNY protein, rather than being localized postsynaptically, may locate to other intracellular compartments by substituting the cysteine residue at position 7 and/or 8 in the amino acid sequence constituting the CCNY protein with serine.

The intracellular compartment may be the trans-Golgi network, endosomes, or endoplasmic reticulum, and more specifically the trans-Golgi network, but is not limited thereto.

As used herein, the term "synapse" refers to a conjunction between an axon end of one neuron and a dendrite of the next neuron, and is divided into pre-synapse and post-synapse.

The present inventors have confirmed the method for targeting CCNY protein to synapses by palmitoylating the cysteine residue at position 7 and/or 8 in the amino acid sequence constituting the CCNY protein, and more specifically have confirmed that the CCNY protein can be localized postsynaptically in the synapses.

As used herein, the term "substitution" refers to the modification of a specific amino acid to an amino acid other than mentioned amino acid, and specifically refers to the modification of one or more cysteines in the amino acid sequence constituting the CCNY protein to an amino acid other than cysteine. More specifically, it refers to the substitution of the cysteine at position 7 and/or 8 with serine or alanine, but is not limited thereto.

The method of substitution may be carried out using a method known to those skilled in the art. Specifically, the substitution of amino acids may be carried out through site-directed mutagenesis involving polymerase chain reaction (PCR) by preparing a primer based on the DNA base sequence.

The site-directed mutagenesis may be induced using a method well known to those skilled in the art, and specifically, the substitution may be carried out using a primer pair based on the DNA sequence encoding the CCNY protein of SEQ ID NO: 1.

As used herein, the term "cognitive function" refers to the ability to efficiently manipulate knowledge and information, and for the purpose of the present invention, the cognitive disease may include a condition caused by a decline in cognitive function, a disease resulting therefrom, and all diseases having the same as a symptom, and specifically, it may refer to a disease caused by damage to brain neurons. The cognitive disease of the present invention may include amnesia, Alzheimer's disease, dementia, Parkinson's disease, and memory disorders, and more specifically, it may be a memory disorder, but is not limited thereto.

Figure 6:
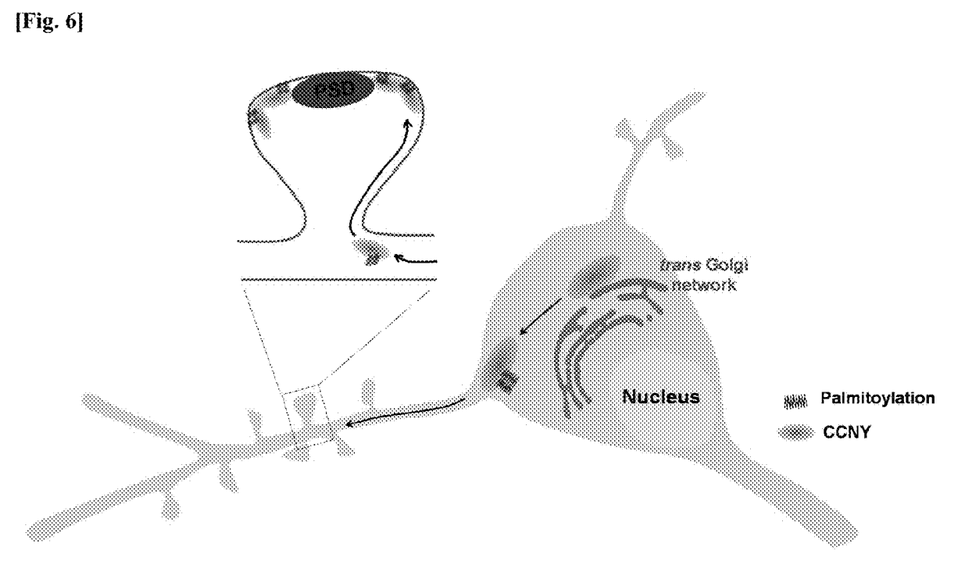
FIG. 6 is a diagram illustrating the model for postsynaptic localization of CCNY which is regulated by palmitoylation, and shows that the palmitoylation of CCNY is a crucial step for the postsynaptic localization of CCNY.

In one specific embodiment of the present invention, it was confirmed that the CCNY protein is associated with the plasma membrane via palmitoylation, and in particular, it was also confirmed that the postsynaptic localization of CCNY protein can be regulated by regulating palmitoylation of C7 and C8 on the CCNY protein (FIG. 6).

These results revealed that the substitution of C7 and C8 cysteines on the CCNY protein with other amino acids blocks palmitoylation, resulting in the localization of CCNY protein into other intracellular compartments rather than being localized postsynaptically, and thus provides an effect of inhibiting the function of the CCNY protein in synapses, thereby implying that it is possible to prevent or treat the cognitive diseases and enhance memory.

BRIEF DESCRIPTION OF DRAWINGS

The patent or application file contains at least one drawing executed in color. Copies of this patent or patent application publication with color drawing(s) will be provided by the Office upon request and payment of the necessary fee.

FIG. 2 shows diagrams illustrating in silico prediction of CCNY palmitoylation. Specifically, (A) shows the predicted scores of palmitoylation site for rat CCNY and PSD-95 using the CSS-Palm program. Note that palmitoylation scores at CCNY (C7 and C8) are similar to those of PSD-95 (C3 and C5). (B) is a schematic illustration showing amino acid sites of CCNY for all cysteine (Cys, C) residues. Note that numbers indicate amino acid residues. (C) shows expression patterns of CCNY-WT-EGFP with or without 2-BP treatment, and other CCNY mutants where each Cys residue indicated in (B) was replaced by serine (Ser, S). The scale bar is 20 μm.

FIG. 3 shows that CCNY is palmitoylated at C7 and C8. Specifically, (A) shows that subcellular localization of CCNY-WT and CCNY-Mut(C7,8S) differ in hippocampal neurons. CCNY-WT-expressing neurons exhibit membrane association and spine enrichment of CCNY, whereas CCNY-Mut(C7,8S)-expressing neurons, which are palmitoylation-deficient mutants, exhibit CCNY accumulation in intracellular compartments and lack of membrane association. All images are single-plane images. The left panel shows the cell body of an EGFP-control-expressing cell. The middle panel shows the cell body (top) and dendritic segment (bottom) of a CCNY-WT-EGFP-expressing cell. The right panel shows the cell body (top) and dendritic segment (bottom) of a CCNY-Mut(C7, 8S)-EGFP-expressing cell. The scale bars are 5 (B and C) show the results of an acyl-biotinyl exchange (ABE) assay. CCNY-WT-EGFP or CCNY-Mut(C7, 8S)-EGFP were overexpressed in HEK293T cells, and the cells were subsequently treated with a palmitoylation blocker, 2-bromopalmitate (2-BP, 30 μM or 100 μM), for 4 hours prior to the ABE assay. As a result, no palmitoylation was detected in the palmitoylation-deficient CCNY-Mut(C7,8S)-expressing or 2-bromopalmitate-treated cells. (C) shows the ABE assay results of PSD-95, used as a positive control.

DETAILED DESCRIPTION OF THE EMBODIMENTS

Hereinafter, the present invention will be described in more detail by way of Examples. However, these Examples are provided for illustrative purposes only, and the scope of the invention is not intended to be limited to or by the Examples.

Example 1. Generation of DNA Constructs

CCNY-WT-EGFP constructs were generated according to the procedures described in a previous study (Cho et al., 2015). Specifically, CCNY-cysteine mutants-EGFP was generated by site-directed mutagenesis (QuickChange Lightning Kit, Agilent Technologies) using CCNY-WT-EGFP as a template, and the sequence changes were verified by sequencing.

Primers used in the generation of palmitoylation-CCNY were as follows:

```
CCNY-C7S-EGFP  (TGC → TCC; Cys → Ser)
F primer
                                         (SEQ ID NO: 2)
5'-GAACACAACTTCGTCCTGCGTGTCGTCCAGCCCTAAG-3'

R primer
                                         (SEQ ID NO: 3)
5'-CTTAGGGCTGGACGACACGCAGGACGAAGTTGTGTTC-3'

CCNY-C8S-EGFP  (TGC → TCC; Cys → Ser)
F primer
                                         (SEQ ID NO: 4)
5'-GAACACAACTTCGTGCTCCGTGTCGTCCAGCCCTAAG-3'

R primer
                                         (SEQ ID NO: 5)
5'-CTTAGGGCTGGACGACACGGAGCACGAAGTTGTGTTC-3'

CCNY-C7,8S-EGFP (TGCTGC → TCCTCC; CysCys → SerSer)
F primer
                                         (SEQ ID NO: 6)
5'-GAACACAACTTCGTCCTCCGTGTCGTCCAGCCCTAAG-3'

R primer
                                         (SEQ ID NO: 7)
5'-CTTAGGGCTGGACGACACGGAGGACGAAGTTGTGTTC-3'
```

Example 2. In Silico Prediction of Palmitoylation Sites

Palmitoylation site prediction of CCNY and PSD-95 was performed using CSS-Palm 2.0 (Ren et al., 2008). The entire FASTA sequences of rat CCNY or PSD-95 were submitted to the CSS-Palm 2.0 interface for the analysis, and palmitoylation prediction scores of the cysteine residues of the protein were obtained.

Example 3. Cell Culture and DNA Transfection

HEK 293T cells were grown in DMEM (Gibco) supplemented with 10% fetal bovine serum. Hippocampal neuronal cultures were prepared from E18 Sprague-Dawley (SD) rat embryos. The hippocampal neurons were grown on poly-D-lysine (50 mg/mL; Sigma)-coated 18 mm glass coverslips and maintained for 10 to 21 days in vitro (DIV) in 12-well plates containing B27 and Glutamax-supplemented Neurobasal medium (Gibco) at 37° C. in an incubator equilibrated with 5% $CO_2$ (Cho et al., 2015). The culture contains glial cells that were grown up to 70% to 80% confluency, where further growth was inhibited by treatment of 5-fluoro-2'-deoxyuridine (FUdR) (50 mg/mL; Sigma).

Neurons were transfected at 10 to 15 DIV using Lipofectamine 2000 (Invitrogen) for 1 to 6 days, and then experiments were performed at 14 to 17 DIV. All experiments handling animals and their embryos were performed in accordance with the guidelines and regulations of the Korea Institute of Science and Technology (KIST). All experimental protocols were approved by the KIST Institutional Animal Care and Use Committee (IACUC; approval number 2018-048).

Example 4. Immunocytochemistry

For staining GM130 and TGN38, hippocampal neurons were fixed with 4% paraformaldehyde/4% sucrose in phosphate-buffered saline (PBS) and permeabilized with 0.1% Triton X-100 in PBS. Then, the cis-Golgi network and trans-Golgi network were labeled with anti-GM130 (BD Transduction Laboratories) and anti-TGN38 (Thermo Scientific), respectively, for 1 hour at room temperature. Neurons were washed and incubated with Cy3-conjugated secondary antibody for 50 minutes at room temperature. Cells were then washed with PBS 4 times and mounted on glass microscope slides in a drop of mounting medium (Thermo) containing DABCO with coverslips and applied to confocal imaging.

For staining endogenous PSD-95, cultured hippocampal neurons grown on the coverslips were fixed with 4% paraformaldehyde/4% sucrose in PBS for 15 minutes at room temperature. Then, cells were permeabilized with 0.1% Triton X-100 in PBS for 10 minutes at room temperature and incubated with mouse anti-PSD-95 (1:200; Thermo MA1-045) mixed with 5% normal donkey serum in PBS for 1 hour at room temperature. After cells were washed 4 times with PBS, they were incubated with Cy3-conjugated anti-mouse secondary antibody for 45 minutes at room temperature. Cells were then washed with PBS, mounted on coverslips, and applied to confocal imaging.

Example 5. Acyl-Biotinyl Exchange (ABE) Assay

The ABE assay was performed as previously described (Wan et al., 2007) with minor modifications. Briefly, HEK293T cells were transfected with CCNY-WT-EGFP, CCNY-Mut(C7,8S)-EGFP, or PSD-95-WT-EGFP. PSD-95-WT-EGFP was transfected with or without DHHC2-HA. Twenty four hours after transfection, the cells were lysed in lysis buffer (150 mM NaCl, 50 mM Tris, 5 mM EDTA, protease inhibitor cocktail, 1 mM PMSF, pH 7.4) with 1.7% Triton X-100 and 10 mM N-ethylmaleimide (NEM) for 1 hour at 4° C. The cell lysates were centrifuged at 250 g for 5 minutes at 4° C., and the resultant supernatants were applied to the chloroform-methanol (CM) precipitation methodology. The precipitated protein pellets were dissolved in 4% SDS buffer (4% SDS, 50 mM Tris, 5 mM EDTA, pH 7.4) with 10 mM NEM for 10 minutes at 37° C. to block free thiol (—SH) groups, and then further incubated overnight in 3 volumes of the lysis buffer containing 0.2% Triton X-100 and 1 mM NEM to further block free thiols, followed by three sequential CM precipitations to remove NEM. The precipitated products were dissolved in 4% SDS buffer for 10 minutes at 37° C. and then incubated in 5 volumes of HA buffer (0.7 M hydroxylamine, 1 mM HPDP-biotin, 0.2% Triton X-100, protease inhibitor cocktail, 1 mM PMSF, pH 7.4) for 1 hour at room temperature to cleave thioester bonds in the palmitoylation modifications by hydroxylamine ($NH_2OH$) and to biotinylate the $NH_2OH$-resultant free thiols with HPDP-biotin, followed by CM precipitation. The precipitated products were dissolved in 4% SDS buffer and incubated in 4 volumes of HPDP-biotin buffer (150 mM NaCl, 50 mM Tris, 5 mM EDTA, 0.2 mM HPDP-biotin, 0.2% Triton X-100, protease inhibitor cocktail, 1 mM PMSF, pH 7.4) for 1 hour at room temperature, followed by an additional CM precipitation. Remaining unreacted HPDP-biotin in the samples was removed by three sequential CM precipitations. Then, the biotinylated protein pellets were dissolved in 2% SDS buffer (2% SDS, 50 mM Tris, 5 mM EDTA, pH 7.4) and incubated in 0.1% SDS buffer supplemented with the lysis buffer containing 0.2% Triton X-100 for 30 minutes at room temperature, followed by a subsequent centrifugation at 15,000 g for 1 minute to remove particulates. The resultant supernatants were incubated with streptavidin-agarose beads for 2 hours at room temperature. After 4 sequential washes with the lysis buffer containing 0.2% Triton X-100 and 0.1% SDS to remove the unbound proteins, the samples were incubated in the lysis buffer containing 0.2% Triton X-100, 0.1% SDS, and 1% β-mercaptoethanol for 15 minutes at 37° C. to elute the bead-bound proteins. The eluted samples in loading buffer (50 mM Tris-HCl, pH 6.8, 5% β-mercaptoethanol, 2% SDS, 0.01% bromophenol blue) were then boiled for 10 minutes at 95° C., applied to SDS-PAGE, and analyzed by immunoreactions with anti-CCNY (Proteintech Group), anti-PSD-95 (Thermo Scientific) and anti-GFP (Roche). The protein bands were obtained by an imaging documentation system (ImageQuant LAS 4000, GE Healthcare) after chemiluminescent reactions (Millipore).

Example 6. Immunoblot Analysis and Antibodies

Samples containing equal amounts of proteins were denatured in SDS sample buffer, subjected to SDS-PAGE, transferred onto a PVDF membrane, and applied to immunoblot analysis. Protein bands on immunoblots were visualized by a chemiluminescence method (Millipore) and an imaging documentation system (ImageQuant LAS 4000, GE Healthcare). Primary antibodies against CCNY (Proteintech Group), GFP (Roche), GM130 (BD Transduction Laboratories), TGN38 (Thermo Scientific), or PSD-95 (Thermo Scientific, 7E3-1B8) were used.

Result 1. Association of CCNY with the Plasma Membrane via Palmitoylation

Figure 1:
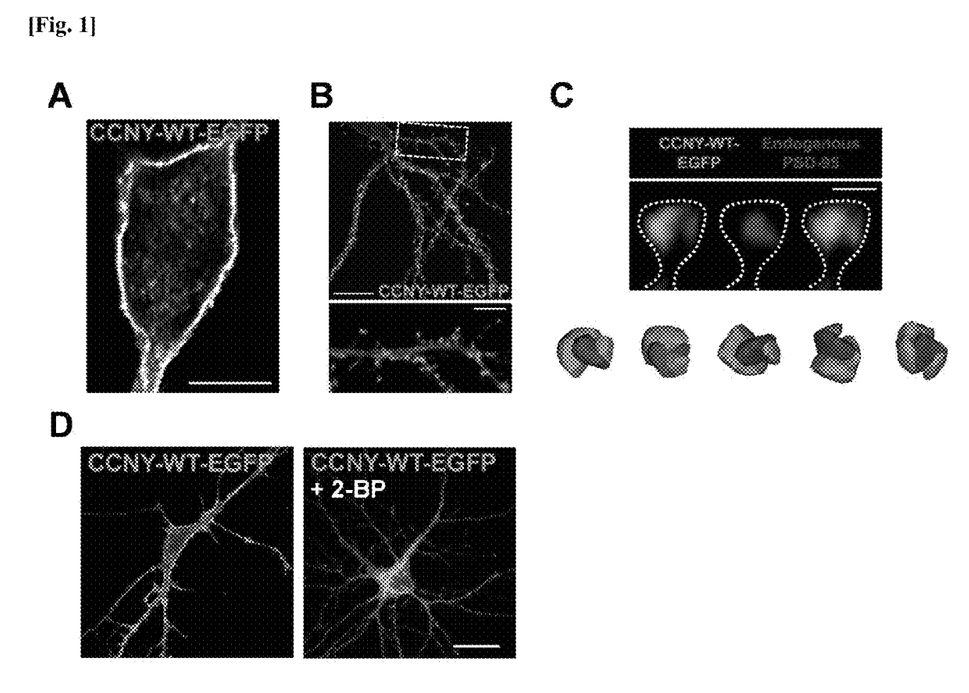
FIG. 1 shows diagrams showing that CCNY is associated with the plasma membrane via palmitoylation and is enriched at dendritic spines. Specifically, (A) is a confocal single-plane image of hippocampal neurons overexpressing EGFP-tagged CCNY-WT. The scale bar is (B) shows a maximum projection image of a neuron expressing CCNY-WT-EGFP (top) and its magnified image on dendritic spines (bottom). The scale bars are 20 μm (top) and 5 μm (bottom). (C) shows co-visualization of CCNY and endogenous PSD-95 at a single-spine level (top), and its 3D volume and iso-surface rendered images presented in various angles (bottom). The scale bar is 1 (D) shows images of neurons overexpressing CCNY-WT-EGFP upon treatment with a palmitoylation blocker, 2-bromopalmitate (2-BP, 100 μM), for 4 hours. The scale bar is 20 μm.

When CCNY is overexpressed in cultured hippocampal neurons, it shows clear localizations at the plasma membrane (FIG. 1A), which resemble the membrane association of a protein by increased hydrophobicity resulting from lipid modifications. In addition, it was confirmed that exogenously expressed CCNY is enriched in the dendritic spines of hippocampal neurons (FIG. 1B). Moreover, the present inventors further examined its postsynaptic localization at the single-spine level by observing its co-localization with endogenous PSD-95, a well-known postsynaptically localized protein (El-Husseini et al., 2000; Kim and Sheng, 2009). As a result, confocal imaging and 3D rendering revealed that CCNY is localized adjacent to endogenous PSD-95 in dendritic spines (FIG. 1C), implying the involvement of CCNY in the regulation of excitatory synapses.

Since CCNY is not a transmembrane protein, it was confirmed that the membrane-associated distribution patterns of CCNY occur through a lipid modification. Interestingly, membrane-associated localization of CCNY-WT-EGFP on the neuronal cell surface was altered in the presence of 2-bromopalmitate (100 μM), a palmitoylation blocker (FIG. 1D), indicating that membrane association of CCNY is due to palmitoylation.

Figure 2:
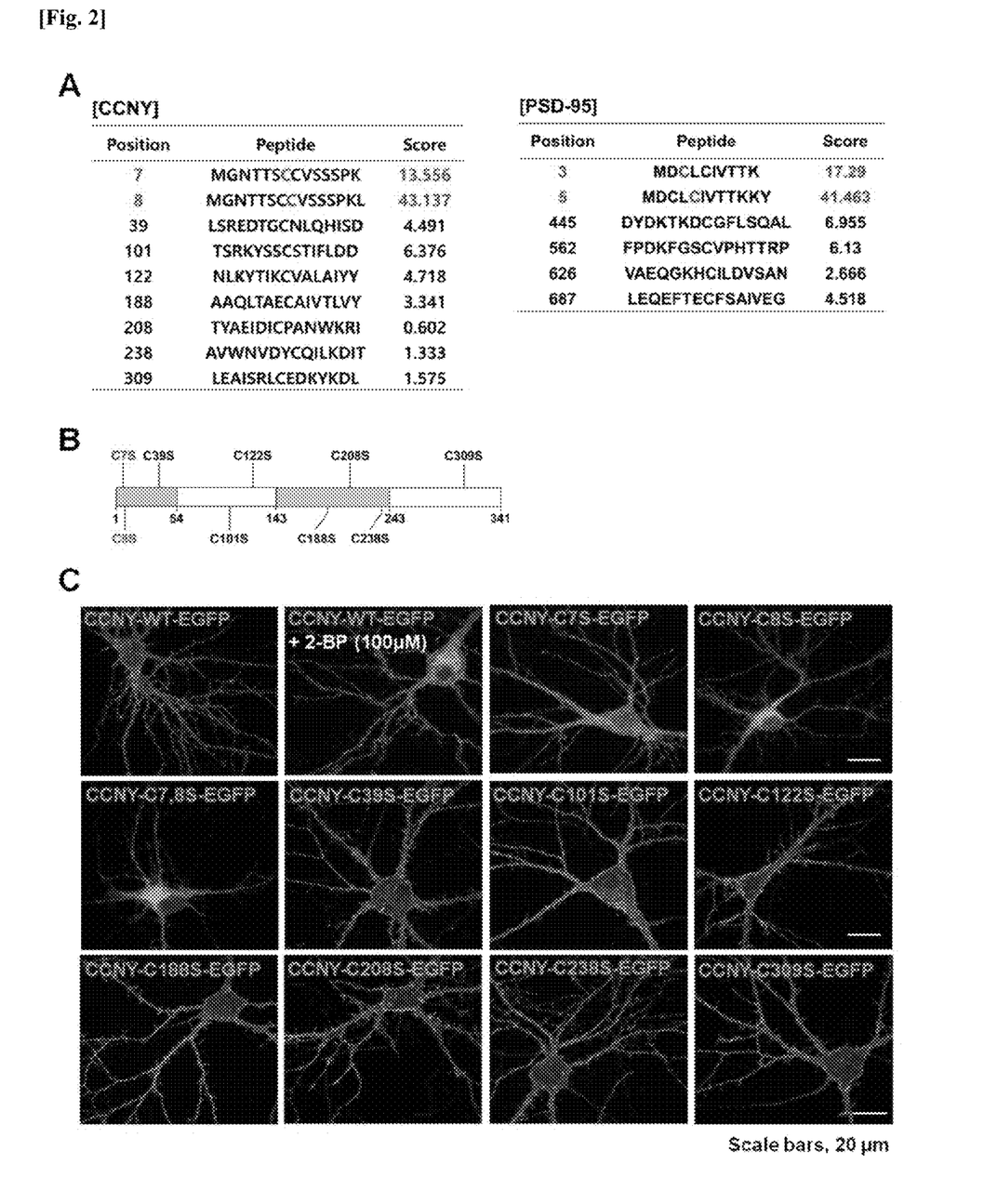

Result 2. In silico Prediction and Biochemical and Imaging Verifications of CCNY Palmitoylation The palmitoylation sites for CCNY were analyzed using CSS-Palm 2.0 (Ren et al., 2008). The result predicted two cysteine residues, C7 and C8, as palmitoylation sites with high CSS-Palm scores (C7, 13.556; C8, 43.137) similar to those of PSD-95 (C3, 17.29; C5, 41.463), which is a well-investigated palmitoylated protein (Topinka and Bredt, 1998; El-Husseini et al., 2000; El-Husseini et al., 2002; El-Husseini and Bredt, 2002) (FIG. 2A). As expected, the cysteine-to-serine mutants of CCNY having high CSS-Palm scores, including CCNY-C7S-EGFP, CCNY-C8S-EGFP, and CCNY-C7,8S-EGFP, were no longer located on the cell surface (FIG. 2C). In contrast, other cysteine-to-serine mutants of CCNY having low CSS-Palm scores, such as CCNY-C39S-EGFP, CCNY-C101S-EGFP, CCNY-C122S-EGFP, CCNY-C188S-EGFP, CCNY-C208S-EGFP, CCNY-C238S-EGFP, or CCNY-C309S-EGFP, were shown to have clear surface localization as CCNY-WT (FIG. 2C), further indicating that CCNY is palmitoylated at residues C7 and C8.

For reference, a double cysteine-to-serine mutant, CCNY-Mut(C7,8S), was used in the present invention (FIG. 3).

Overexpression of CCNY-Mut(C7,8S) in cultured hippocampal neurons drastically reduced the plasma membrane association of CCNY and induced its accumulation in intracellular compartments, while showing a reduced spine localization of CCNY compared to CCNY-WT (FIG. 3A). Altered protein localization of palmitoylation-deficient CCNY protein to intracellular compartments due to mutations in these two cysteine residues further supports that the enrichment of CCNY in the dendritic spines and the association thereof with the plasma membrane are due to palmitoylation of CCNY.

Acyl-biotinyl exchange (ABE) assay, a popular assay to detect protein palmitoylation, revealed that CCNY-WT-EGFP is palmitoylated, and the palmitoylation is blocked in the presence of 2-bromopalmitate (30 μM, 100 μM), while CCNY-Mut(C7,8S)-EGFP is not palmitoylated in the absence of 2-bromopalmitate (FIG. 3B), indicating that CCNY is palmitoylated at residues C7 and C8. In addition, palmitoylation of PSD-95 was observed as a positive control for the palmitoylation assay, and this palmitoylation was also inhibited by 2-bromopalmitate (FIG. 3C).

Figure 4:
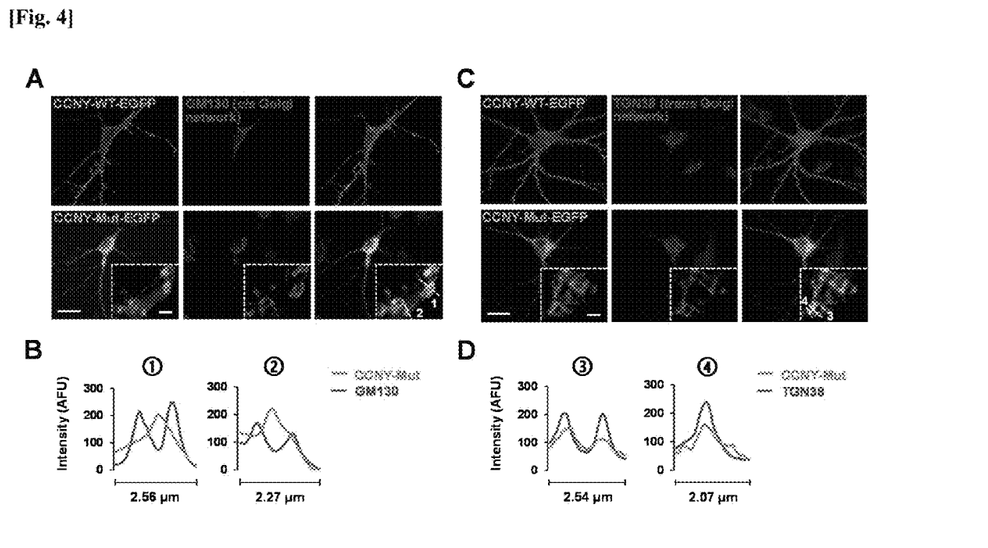
FIG. 4 shows that palmitoylation-deficient CCNY is stuck on the trans-Golgi network but not on the cis-Golgi network. Specifically, neurons overexpressing CCNY-WT-EGFP or CCNY-Mut(C7,8S)-EGFP were immunostained with anti-GM130 to label the cis-Golgi network (A) or with anti-TGN38 to label the trans-Golgi network (C). Line scan analyses are shown in (B) and (D). The scale bars are 20 μm and 2 μm for low- and high-magnification images, respectively.

Result 3. Regulation of Postsynaptic Localization of CCNY via CCNY Palmitoylation The identity of the intracellular compartments, in which the palmitoylation-deficient CCNY-Mut(C7,8S) proteins are stuck, was confirmed by immunocytochemistry and a high-resolution imaging technique. The results revealed that palmitoylation-deficient CCNY colocalizes with the trans-Golgi network (FIGS. 4C and 4D), but not with the cis-Golgi network (FIGS. 4A and 4B).

Figure 5:
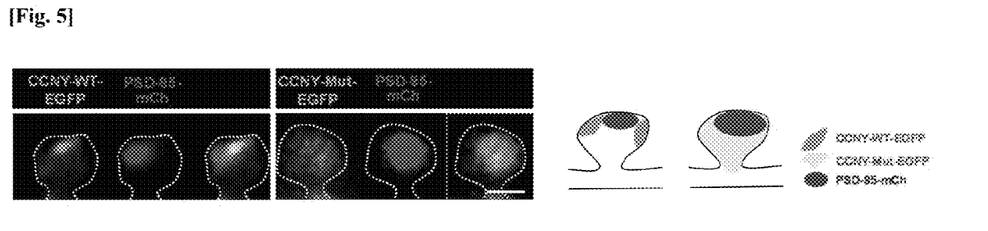
FIG. 5 shows that palmitoylation-deficient CCNY alters the postsynaptic localization of CCNY. Specifically, hippocampal neurons were co-expressed with EGFP-tagged CCNY-WT or CCNY-Mut(C7,8S) and mCherry-tagged PSD-95. Images were analyzed to single-spine levels, and the results revealed that the postsynaptic localization of CCNY-WT adjacent to PSD-95 was altered by palmitoylation deficiency of CCNY-Mut(C7,8S). The scale bar is 1 μm.

Consistent with this altered localization of palmitoylation-deficient CCNY to the trans-Golgi network, the palmitoylation-deficient mutant of CCNY no longer exists in the spine adjacent to the PSD, but instead diffuses into the cytosol within the spine when observed at the single-spine level (FIG. 5).

Taken together, the palmitoylation of CCNY, a novel postsynaptic protein known to be implicated in synaptic plasticity and learning and memory, is a critical process for CCNY to be localized in the postsynaptic spines, thereby confirming that it has an important role in CCNY synapses by regulating the localization of CCNY via palmitoylation (FIG. 6).

The detailed description of contents which can be fully recognized and inferred by those skilled in the technical field to which the present invention pertains has been omitted, and it will be understood that various modifications are possible without departing from the technical spirit or essential characteristics of the present invention, in addition to specific embodiments disclosed herein. Therefore, it will be understood by those skilled in the art that the present invention may be implemented in a specific form contrary to what is specifically described and illustrated herein.

The invention claimed is:

1. A method for regulating targeting of Cyclin Y (CCNY) protein to a synapse in vitro, comprising contacting the CCNY protein with a palmitoyl acyltransferase resulting in palmitoylation of CCNY, wherein the palmitoylation involves addition of a palmitoyl group to the cysteine residue at position 7 or 8 in the amino acid sequence of the CCNY protein, and whereby the CCNY protein is targeted to the synapse.

2. The method of claim 1, wherein the CCNY protein is localized postsynaptically.

3. The method of claim 1, wherein the CCNY protein consists of the amino acid sequence of SEQ ID NO: 1.

* * * * *